US009405886B2

(12) United States Patent
Taylor et al.

(10) Patent No.: US 9,405,886 B2
(45) Date of Patent: Aug. 2, 2016

(54) METHOD FOR DETERMINING CARDIOVASCULAR INFORMATION

(75) Inventors: Charles A Taylor, Menlo Park, CA (US); Hyun Jin Kim, Boulder, CO (US); Jessica S. Coogan, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 403 days.

(21) Appl. No.: 12/661,491

(22) Filed: Mar. 17, 2010

(65) Prior Publication Data

US 2010/0241404 A1    Sep. 23, 2010

Related U.S. Application Data

(60) Provisional application No. 61/210,401, filed on Mar. 17, 2009.

(51) Int. Cl.
*G06F 19/16* (2011.01)
*G06F 19/00* (2011.01)

(52) U.S. Cl.
CPC ................................. *G06F 19/3437* (2013.01)

(58) Field of Classification Search
None
See application file for complete search history.

(56) References Cited

U.S. PATENT DOCUMENTS

| | | | |
|---|---|---|---|
| 6,117,087 | A | 9/2000 | Kamm |
| 6,236,878 | B1 | 5/2001 | Taylor |
| 7,191,110 | B1 | 3/2007 | Charbel |
| 2007/0163353 | A1* | 7/2007 | Lec et al. ................... 73/700 |

OTHER PUBLICATIONS

Computational Analysis of Flow in a Curved Tube Model of the Coronary Arteries: Effects of Time-varying Curvature. Santamarina et al., Annals of Biomedical Engineering, 26:944-954, 1998.
Computational simulation of intracoronary flow based on real coronary geometry, Boutsianis et al., European Journal of Cardio-thoracic Surgery 26:248-256, 2004.
Coupling between lumped and distributed models for blood flow problems, Quarteroni et al., Comput Visual Sci 4: 111-124, 2001.
Experimental and Computational Flow Evaluation of Coronary Stents, Berry et al., Annals of Biomedical Engineering, 28:386-398, 2000.
Factors Influencing Blood Flow Patterns in the Human Right Coronary Artery, Myers et al., Annals of Biomedical Engineering, 29:109-120, 2001.
Multiscale modeling of the cardiovascular system: applicationtothestudyofpulmonaryandcoronary perfusions in the univentricular circulation, Lagana et al., Journal of Biomechanics 38:1129-1141, 2005.
Numerical Simulation of Pulsatile Flow in a Compliant Curved Tube Model of a Coronary Artery, Qiu et al., Journal of Biomechanical Engineering 122:77-85, 2000.
Numerical Treatment of Defective Boundary Conditions for the Navier-Stokes Equations, Formaggia et al., Siam J. Numer. Anal. 40(1),:376-401, 2002.
Strain distribution over plaques in human coronary arteries relates to shear stress, Gijsen et al., Am J Physiol Heart Circ Physiol 295: H1608-H1614, 2008.
Validated computation of physiologic flow in a realistic coronary artery branch, Perktold et al., Journal of Biomechanics 31:217-228, 1998.

* cited by examiner

*Primary Examiner* — Pablo S Whaley
(74) *Attorney, Agent, or Firm* — Bookoff McAndrews, PLLC (57) ABSTRACT

A noninvasive patient-specific method is provided to aid in the analysis, diagnosis, prediction or treatment of hemodynamics of the cardiovascular system of a patient. Coronary blood flow and pressure can be predicted using a 3-D patient image-based model that is implicitly coupled with a model of at least a portion of the remaining cardiovascular system. The 3-D patient image-based model includes at least a portion of the thoracic aorta and epicardial coronaries of the patient. The shape of one or more velocity profiles at the interface of the models is enforced to control complex flow features of recirculating or retrograde flow thereby minimizing model instabilities and resulting in patient-specific predictions of coronary flow rate and pressure. The invention allows for patient-specific predictions of the effect of different or varying physiological states and hemodynamic benefits of coronary medical interventions, percutaneous coronary interventions and surgical therapies.

12 Claims, 3 Drawing Sheets

FIGURE 3   A: Inlet - coupled to lumped parameter heart model

FIGURE 4   B-H: Outlets - coupled to three-element Windkessel models

FIGURE 5   a-k: Coronary outlets - coupled to lumped parameter coronary vascular models

METHOD FOR DETERMINING CARDIOVASCULAR INFORMATION

CROSS-REFERENCE TO RELATED APPLICATIONS

This application claims priority from U.S. Provisional Patent Application No. 61/210,401 filed Mar. 17, 2009, which is incorporated herein by reference.

STATEMENT OF GOVERNMENT SPONSORED SUPPORT

This invention was made with Government support under contract 0205741 awarded by National Science Foundation (NSF). The Government has certain rights in this invention.

FIELD OF THE INVENTION

This invention relates to computer-implemented methods of quantifying and predicting hemodynamic aspects of the cardiovascular system to aid in the diagnosis and treatment of coronary diseases.

BACKGROUND

The number of patients with coronary artery disease continues to rise resulting in a third of global deaths and afflicting over seventeen million individuals in the United States alone. Once patients are diagnosed with coronary artery disease using medical imaging techniques including angiography, ultrasound, and computed tomography, they are treated with medications, lifestyle changes, interventional procedures, or open heart surgery depending on the severity of their disease. Flow rate and pressure in coronary arteries are measured invasively during interventional procedures or open heart surgery. However, the information obtainable from the medical imaging techniques and the invasive flow and pressure measurement techniques are limited because the resolution of the medical imaging techniques are sufficient to visualize only the larger arteries, and the flow and pressure measurement techniques are highly invasive and restricted by time and the physical condition of the patient. However, information on coronary flow rate and the pressure of the coronary vascular beds of a patient is crucial to select treatments.

Computational simulations have proven to be useful in studying blood flow in the cardiovascular system and include research on the hemodynamics of healthy and diseased blood vessels, the design and evaluation of cardiovascular medical devices, planning of cardiovascular surgeries, and the prediction of the outcomes of interventions. However, computational simulations have been rarely used to predict pulsatile velocity and pressure fields of three-dimensional coronary vascular beds, in part because the flow rate and pressure in the coronary vascular beds are highly related to the interactions between the heart and the arterial system. Unlike flow in other parts of the arterial system, coronary flow decreases when the ventricles contract, increasing the intramyocardial pressure. Coronary flow increases when the ventricles relax, thereby, decreasing the intramyocardial pressure. Therefore, to model coronary flow and pressure realistically, it is necessary to have a model of the heart and a model of the arterial system with consideration of the interactions between the two models.

Because of this complexity in modeling coronary flow and pressure, most three-dimensional computational studies have been conducted with coronary arteries only, ignoring the interactions between the heart and the arterial system and prescribing, not predicting, coronary flow. Further, these studies have not modeled realistic pressures and generally use traction-free outlet boundary conditions. The analytic models used as boundary conditions were coupled explicitly, necessitating either sub-iterations within the same time step or a small time step size bounded by the stability of an explicit time integration scheme. To predict the flow rate and the pressure in the coronary arterial trees of a patient realistically, computational simulations should be robust and stable enough to handle complex flow characteristics, and the coupling should be efficient and versatile to different scales of computer models.

In view of the above, there remains a need in the art for new and improved techniques for more realistic computer models of coronary flow rate and pressure.

SUMMARY OF THE INVENTION

The invention provides a noninvasive patient-specific method for aiding in the analysis, diagnosis, prediction or treatment of hemodynamics of the cardiovascular system of a patient. Coronary blood flow and pressure can be predicted using a 3-D patient image-based model that is implicitly coupled with a model of at least a portion of the remaining cardiovascular system (e.g. a lumped parameter heart model, a lumped parameter systemic vascular model, a lumped parameter pulmonary vascular model, or any combination thereof). Implicit coupling between the models in this invention is defined as the simultaneous solution at each instant of time of the equations of blood flow in both the 3-D patient image-based model and the model for at least a portion of the remainder of the cardiovascular system. The 3-D patient image-based model includes at least a portion of the thoracic aorta of the patient and at least a portion of the epicardial coronary arteries of the patient. 3-D anatomical and/or physiological data for the 3-D patient-image based model is preferably obtained via non-invasive imaging techniques or systems such as, but not limited to, computed tomography or magnetic resonance imaging. The shape of one or more shape velocity profiles at the interface of the models is enforced to have a predetermined form to control recirculating flow features or retrograde flow to minimize model instabilities and resulting in patient-specific predictions of coronary flow rate and pressure. The invention, which is implemented in a computer system, allows for patient-specific predictions of coronary flow rate and pressure under different or varying physiological states (e.g. rest, exercise, pharmacologic-induced stress, or the like) and by simulating one or more hemodynamic benefits of coronary medical interventions, percutaneous coronary interventions and surgical therapies.

DETAILED DESCRIPTION

Methods to calculate flow and pressure in three-dimensional coronary vascular beds are provided by considering a hybrid numerical/analytic closed loop system. For each coronary outlet of the three-dimensional finite element model, a lumped parameter coronary vascular bed model was coupled and the impedance of downstream coronary vascular networks not modeled explicitly in the computational domain was approximated. Similarly, Windkessel models were assigned to the upper branch vessels and the descending thoracic aorta to represent the rest of the arterial system. For the inlet, a lumped parameter heart model was coupled that completes a closed-loop description of the system. Using the heart model, it is possible to compute the compressive forces acting on the coronary vascular beds throughout the cardiac cycle. Further, the shape of velocity profiles of the inlet and outlet boundaries with retrograde flow was enforced to minimize numerical instabilities. The computer models solved for coronary flow and pressure as well as aortic flow and pressure in subject-specific models by considering the interactions between these model of the heart, the impedance of the systemic arterial system and the pulmonary system, and the impedance of coronary vascular beds.

Three-Dimensional Finite Element Model of Blood Flow and Vessel Wall Dynamics

Blood flow in the large vessels of the cardiovascular system can be approximated by a Newtonian fluid. Blood flow can then be solved using the incompressible Navier-Stokes equations and the motion of the vessel wall was modeled using the elastodynamics equations.

For a fluid domain $\Omega$ with boundary $\Gamma$ and solid domain $\Omega^s$ with boundary $\Gamma^s$, we solve for velocity $\vec{v}(\vec{x}, t)$, pressure $p(\vec{x},t)$, and wall displacement $\vec{u}(\vec{x}^s, t)$ as follows:

Given $\vec{f}: \Omega \times (0,T) \to \mathbb{R}^3$, $\vec{f}^s: \Omega^s \times (0,T) \to \mathbb{R}^3$, $\vec{g}: \Gamma_g \times (0,T) \to \mathbb{R}^3$, $\vec{g}^s: \Gamma_g^s \times (0,T) \to \mathbb{R}^3$, $\vec{v}_0: \Omega \to \mathbb{R}^3$, $\vec{u}_0: \Omega^s \to \mathbb{R}^3$, and $\vec{u}_{0,t}: \Omega^s \to \mathbb{R}^3$, find $\vec{v}(\vec{x},t)$, $p(\vec{x},t)$, and $\vec{u}(\vec{x}^s,t)$ for $\forall \vec{x} \in \Omega$, $\forall \vec{x}^s \in \Omega^s$, and $\forall t \in (0,T)$, such that the following conditions are satisfied:

$$\rho \vec{v}_{,t} + \rho \vec{v} \cdot \nabla \vec{v} = -\nabla p + div(\tau) + \vec{f} \text{ for } (\vec{x}, t) \in \Omega \times (0, T) \quad (1)$$

$$div(\vec{v}) = 0 \text{ for } (\vec{x}, t) \in \Omega \times (0, T)$$

$$\rho^s \vec{u}_{,tt} = \nabla \cdot \sigma^s + \vec{f}^s \text{ for } (\vec{x}^s, t) \in \Omega^s \times (0, T)$$

where $\tau = \mu(\nabla \vec{v} + (\nabla \vec{v})^T)$ and $\sigma^s = C : \frac{1}{2}(\nabla \vec{u} + (\nabla \vec{u})^T)$ with the Dirichlet boundary conditions, $$\vec{v}(\vec{x},t) = \vec{g}(\vec{x},t) \text{ for } (\vec{x},t) \in \Gamma_g \times (0,T)$$

$$\vec{u}(\vec{x}^s,t) = \vec{g}^s(\vec{x}^s,t) \text{ for } (\vec{x}^s,t) \in \Gamma_g^s \times (0,T) \quad (2)$$

the Neumann boundary conditions, $$\vec{t}_{\vec{n}} = [-pI+\tau]\vec{n} = \vec{h}(\vec{v},p,\vec{x},t) \text{ for } \vec{x} \in \Gamma_h \quad (3)$$

and the initial conditions, $$\vec{v}(\vec{x},0) = \vec{v}_0(\vec{x}) \text{ for } \vec{x} \in \Omega$$

$$\vec{u}(\vec{x}^s,0) = \vec{u}_0(\vec{x}^s) \text{ for } \vec{x}^s \in \Omega^s$$

$$\vec{u}_{,t}(\vec{x}^s,0) = \vec{u}_{0,t}(\vec{x}^s) \text{ for } \vec{x}^s \in \Omega^s \quad (4)$$

For fluid-solid interface conditions, the conditions implemented in the coupled momentum method were used with a fixed fluid mesh assuming small displacements of the vessel wall.

The density $\rho$ and the dynamic viscosity $\mu$ of the fluid, and the density $\rho^s$ of the vessel walls are assumed to be constant. The external body force on the fluid domain is represented by $\vec{f}$. Similarly, $\vec{f}^s$ is the external body force on the solid domain, $C$ is a fourth-order tensor of material constants, and $\sigma^s$ is the vessel wall stress tensor.

A stabilized semi-discrete finite element method was utilized to use the same order piecewise polynomial spaces for velocity and pressure variables.

Boundary Conditions

The boundary $\Gamma$ of the fluid domain is divided into a Dirichlet boundary portion $\Gamma_g$ and a Neumann boundary portion $\Gamma_h$. Further, the Neumann boundary portion $\Gamma_h$ is divided into coronary surfaces $\Gamma_{h_{cor}}$, inlet surface $\Gamma_{in}$, and the set of other outlet surfaces $\Gamma'_h$, such that $\overline{(\Gamma_{h_{cor}} \cup \Gamma_{in} \cup \Gamma'_h)} = \Gamma_h$ and $\Gamma_{h_{cor}} \cap \Gamma_{in} \cap \Gamma'_h = \phi$. Note that in this example, when the aortic valve is open, the inlet surface is included in the Neumann boundary portion $\Gamma_h$, not in the Dirichlet boundary portion $\Gamma_g$, to enable coupling with a lumped parameter heart model. Therefore, the Dirichlet boundary portion $\Gamma_g$ only includes the inlet and outlet rings of the computational domain when the aortic valve is open. These rings are fixed in time and space.

Boundary Conditions for Coronary Outlets

To represent the coronary vascular beds absent in the computational domain, a lumped parameter coronary vascular model was used (FIGS. 2-5). The coronary venous microcirculation compliance was eliminated from the original model to simplify the numerics without affecting the shape of the flow and pressure waveforms significantly. Each coronary vascular bed model includes coronary arterial resistance $R_a$, coronary arterial compliance $C_a$, coronary arterial microcirculation resistance $R_{a\text{-}micro}$, myocardial compliance $C_{im}$, coronary venous microcirculation resistance $R_{v\text{-}micro}$, coronary venous resistance $R_v$, and intramyocardial pressure $P_{im}(t)$.

For each coronary outlet $\Gamma_{h_{cor_k}}$ of the three-dimensional finite element model where $$\Gamma_{h_{cor_k}} \subseteq \Gamma_{h_{cor}},$$

the lumped parameter coronary vascular model was implicitly coupled using the continuity of mass and momentum operators of the coupled multidomain method as follows:

$$[M_m(\vec{v}, p) + H_m] = \qquad (5)$$

$$-\left(R\int_{\Gamma_{h_{cor_k}}} \vec{v}(t) \cdot \vec{n} d\Gamma + \int_0^t e^{\lambda_1(t-s)} Z_1 \int_{\Gamma_{h_{cor_k}}} \vec{v}(s) \cdot \vec{n} d\Gamma ds\right) l +$$

$$\left(\int_0^t e^{\lambda_2(t-s)} Z_2 \int_{\Gamma_{h_{cor_k}}} \vec{v}(s) \cdot \vec{n} d\Gamma ds - \vec{n} \cdot \tau \cdot \vec{n}\right) l +$$

$$\tau - (A e^{\lambda_1 t} + B e^{\lambda_2 t}) l -$$

$$\left(\int_0^t e^{\lambda_1(t-s)} \cdot Y_1 P_{im}(s) ds + \int_0^t e^{\lambda_2(t-s)} \cdot Y_2 P_{im}(s) ds\right) l$$

$$[\vec{M}_c(\vec{v}, p) + \vec{H}_c] = \vec{v}$$

where the parameters R, $Z_1$, $Z_2$, A, B, $Y_1$, $Y_2$, $\lambda_1$, $\lambda_2$ are derived from the lumped parameter coronary vascular models.

Figure 1:
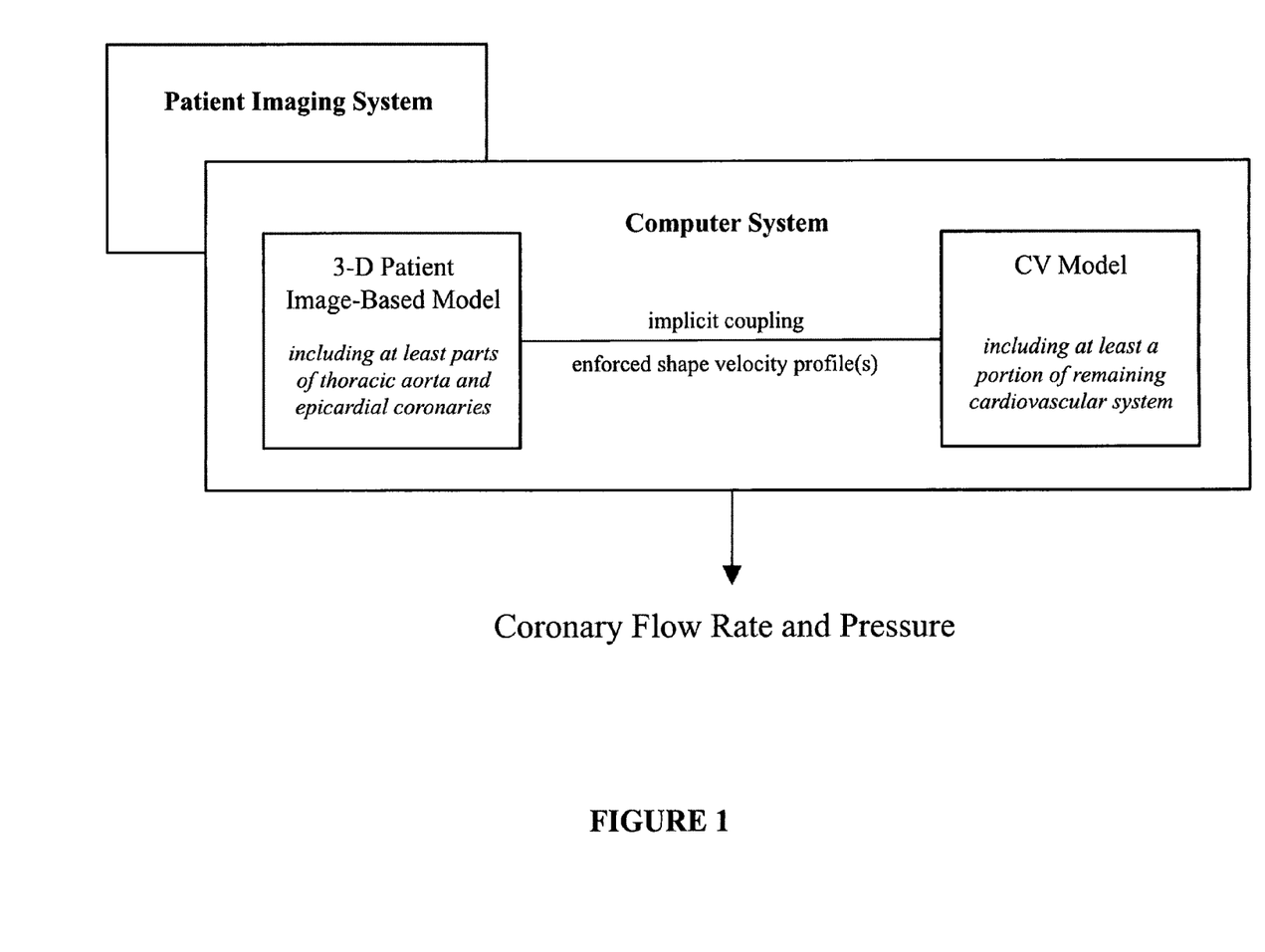
FIG. 1 shows a method and system according to an embodiment of the invention including a patient imaging system either directly or indirectly coupled to a computer system providing 3-D patient images for the 3-D patient image-based model. The 3-D patient image-based model is implicitly coupled to a model of at least a portion of the remaining cardiovascular (CV) system. The shape of at least one of the velocity profiles is enforced at the interface between the models. Coronary blood flow rate and pressure is calculated using the computer-implemented models and displayed or outputted in computer graphics or data.
Figure 2:
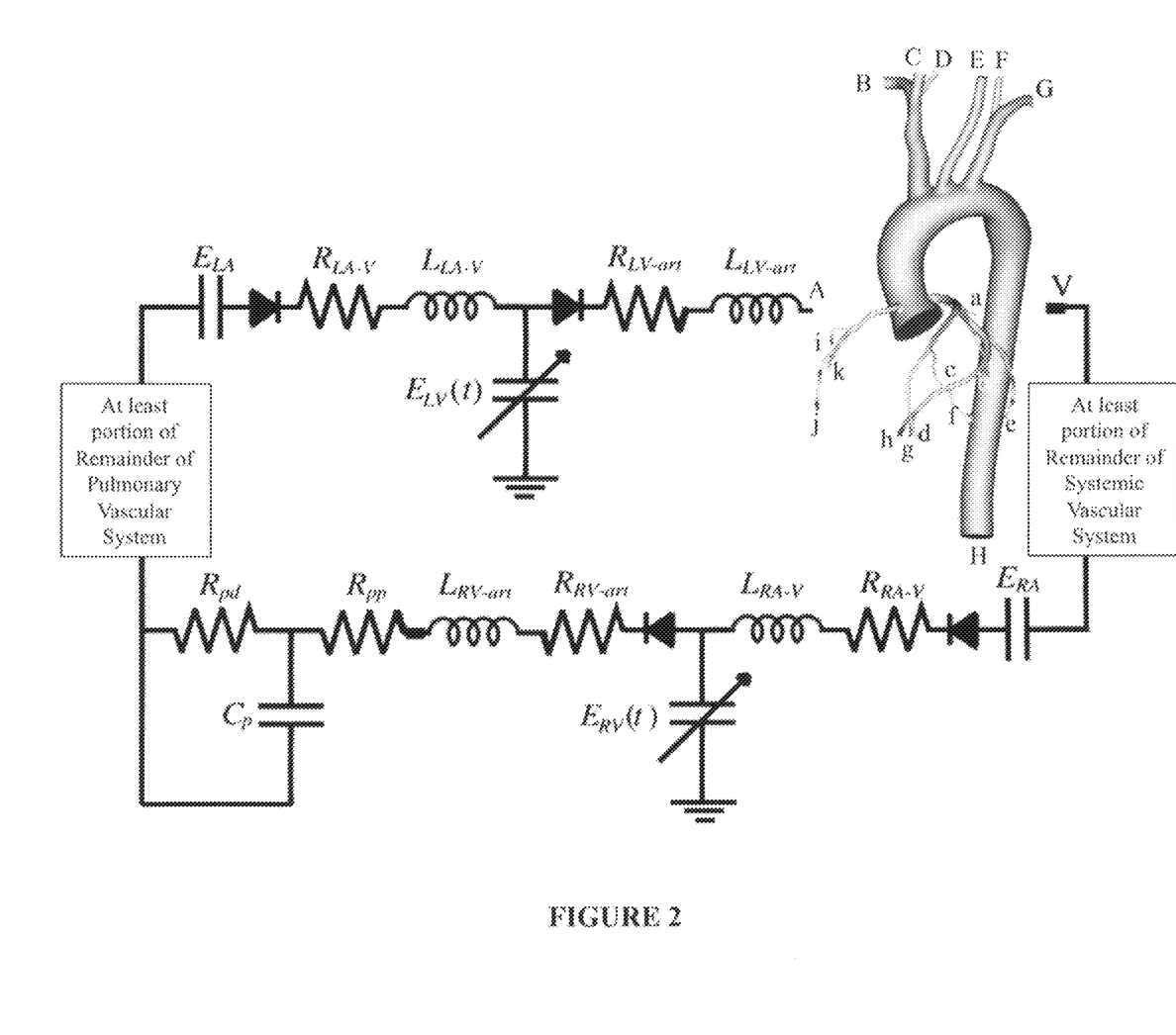
FIG. 2 is a schematic of a model of the cardiovascular system according to an embodiment of the invention including lumped parameter models of the right and left atria and ventricles. The aortic inlet is coupled to the lumped parameter model of the left ventricle at (A). All the outlets of the three-dimensional computational model feed back in the lumped model at (V). The lumped parameter models coupled to the inlet, upper branch vessels, the descending thoracic aorta, and coronary outlets for simulations of blood flow in a normal thoracic aorta model with coronary outlets under rest and exercise conditions are shown on the right. Note that all the outlets of the three-dimensional computational model feed back in the lumped model at (V).
Figure 3:
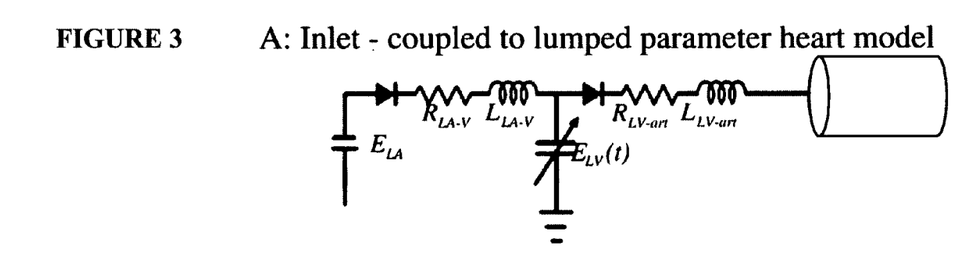
FIG. 3 shows inlet A coupled to a lumped parameter heart model according to an embodiment of the invention.
Figure 4:
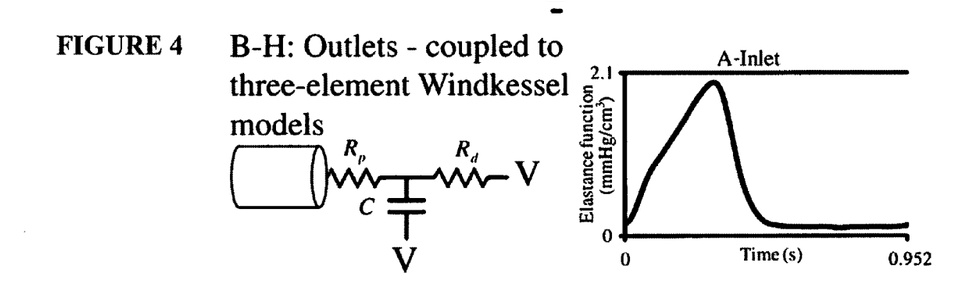
FIG. 4 shows outlets B-H coupled to three-element Windkessel models according to an embodiment of the invention.
Figure 5:
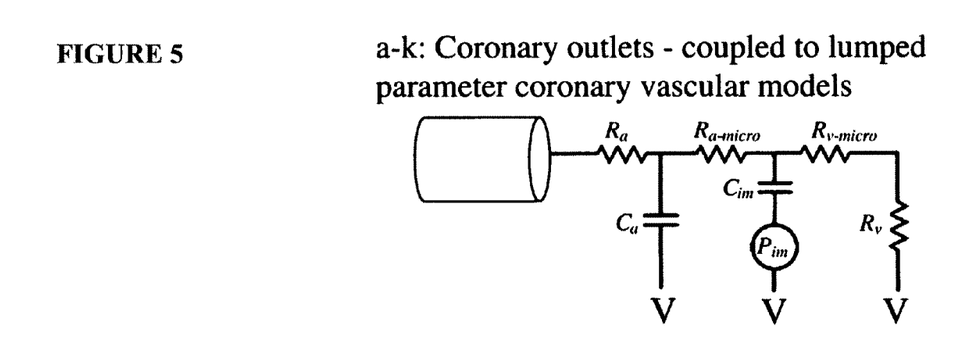
FIG. 5 shows coronary outlets a-k coupled to lumped parameter coronary vascular models according to an embodiment of the invention.

The intramyocardial pressure $P_{im}$ representing the compressive force acting on the coronary vessels due to the contraction and relaxation of the left and right ventricles was modeled with either the left or right ventricular pressure depending on the location of the coronary arteries. Both the left and right ventricular pressures were computed from two lumped parameter heart models of the closed loop system (FIGS. 2-3).

Boundary Conditions for the Inlet

The left and right sides of the heart were modeled using a lumped parameter heart model. Each heart model includes a constant atrial elastance $E_A$, atrio-ventricular valve, atrioventricular valvular resistance $R_{A-V}$, atrio-ventricular inductance $L_{A-V}$, ventriculo-arterial valve, ventriculo-arterial valvular resistance $R_{V-art}$, ventriculo-arterial inductance $L_{V-art}$, and time-varying ventricular elastance E(t). An atrio-ventricular inductance $L_{A-V}$ and ventriculo-arterial inductance $L_{V-art}$ were added to the model to approximate the inertial effects of blood flow.

The time-varying elastance E(t) models the contraction and relaxation of the left and right ventricles. Elastance is the instantaneous ratio of ventricular pressure $P_v(t)$ and ventricular volume $V_v(t)$ according to the following equation:

$$P_v(t) = E(t) \cdot [V_v(t) - V_0] \qquad (6)$$

Here, $V_0$ is a constant correction volume, which is recovered when the ventricle is unloaded.

Each elastance function is derived by scaling a normalized elastance function, which remains unchanged regardless of contractility, vascular loading, heart rate and heart disease to approximate the measured cardiac output, pulse pressure and contractility of each subject.

The left side of the heart lumped parameter model is coupled to the inlet of the finite element model using a coupled multidomain method when the aortic valve is open as follows:

$$[M_m(\vec{v}, p) + H_m]_{\Gamma_{in}} = \qquad (7)$$

$$-E(t) \cdot \left\{V_v(t_{ao,LV}) + \int_{t_{ao,LV}}^t \int_{\Gamma_{in}} \vec{v} \cdot \vec{n} d\Gamma ds - V_{LV,0}\right\} l -$$

$$\left(R_{LV-art} + L_{LV-art}\frac{d}{dt}\right) \int_{\Gamma_{in}} \vec{v} \cdot \vec{n} d\Gamma l + \tau - (\vec{n} \cdot \tau \cdot \vec{n}) l$$

$$[\vec{M}_c(\vec{v}, p) + \vec{H}_c]_{\Gamma_{in}} = \vec{v}\big|_{\Gamma_{in}}$$

Here, $t_{ao,LV}$ is the time the aortic valve opens. When the valve is closed, the inlet boundary is switched to a Dirichlet boundary and assigned a zero velocity condition.

Boundary Conditions for Other Outlets

For the other boundaries $\Gamma'_h$, we used the same method to couple three-element Windkessel models and modeled the continuity of momentum and mass using the following operators:

$$[M_m(\vec{v}, p) + H_m]_{\Gamma'_h} =$$

$$-\left\{R_p \int_{\Gamma'_h} \vec{v} \cdot \vec{n} ds + (R_p + R_d) \int_0^t \frac{e^{-(t-t_1)/\tau}}{C} \int_{\Gamma'_h} \vec{v} \cdot \vec{n} ds dt_1\right\} l +$$

$$\left\{\left(P(0) - R\int_{\Gamma'_h} \vec{v}(0) \cdot \vec{n} ds - P_d(0)\right) e^{-t/\tau} - P_d(t)\right\} l + \tau - \vec{n} \cdot \tau \cdot \vec{n} l$$

$$[\vec{M}_c(\vec{v}, p) + \vec{H}_c]_{\Gamma'_h} = \vec{v}$$

Closed Loop Model

The boundary conditions combined with the three-dimensional finite element model of the aorta may include a closed loop model of the cardiovascular system. In most cases, the closed loop model has two lumped parameter heart models representing the left and right sides of the heart, a three-dimensional finite element model of the aorta with coronary arteries, three-element Windkessel models and lumped parameter coronary vascular models that represent the rest of the systemic circulation, and a lumped parameter model to approximate the pulmonary circulation. This closed loop model can be used to compute the right ventricular pressure, which is used to approximate the intramyocardial pressure acting on the right coronary arteries.

Parameter Values

Choice of the Parameter Values for Coronary Boundary Conditions

The boundary condition parameters determining the mean flow to each primary branch of the coronary arteries can be determined using morphology data and data from the literature. In one example, the mean coronary flow was assumed to be 4.0% of the cardiac output. For each coronary outlet surface, coronary venous resistance was calculated on the basis of the mean flow and assigned venous pressure according to literature data. The coronary arterial resistance and coronary arterial microcirculation resistance was obtained on the basis of mean flow, mean arterial pressure, and the coronary impedance spectrum using literature data. The capacitance values were adjusted to give physiologically realistic coronary flow and pressure waveforms.

In an example during simulated exercise, the mean flow to the coronary vascular bed was increased to maintain the mean flow at 4.0% of the cardiac output. The coronary parameter values for each coronary outlet surface were modified by increasing the capacitances, and the ratio of the coronary arterial resistance to the total coronary resistance.

Choice of the Parameter Values for the Inflow Boundary Condition

The parameter values of the lumped parameter heart model according to one example were determined as follows:

$$t_{max,LV} = t_{max,RV}$$

$$= \begin{cases} \dfrac{T}{3}, & \text{at rest, where } T \text{ is the measured cardiac cycle.} \\ 0.5T, & \text{during exercise.} \end{cases}$$

$$E_{max,LV} = \frac{\gamma \cdot R_S}{T},$$

where $R_S$ is total resistance of systemic circulation and $1 \leq \gamma \leq 2$.

$$E_{max,RV} = \frac{\gamma \cdot R_P}{T},$$

where $R_P$ is total resistance of pulmonary circulation and $1 \leq \gamma \leq 2$.

$$V_{LV,0} = V_{LV,esv} - \frac{0.9 P_{sys}}{E_{max,LV}},$$

where $V_{LV,esv}$ is an end-systolic volume of left ventricle and $P_{sys}$ is an aortic systolic pressure.

Choice of the Parameter Values for Other Outlet Boundary Conditions

For the upper branch vessels and the descending thoracic aorta in one model, three-element Windkessel models were adjusted to match mean flow distribution and the measured brachial artery pulse pressure by modifying the total resistance, capacitance, and the ratio between the proximal resistance and distal resistance based on literature data.

Constraining Shape of Velocity Profiles to Stabilize Blood Flow Simulations

Using these sets of boundary conditions, in one example, the physiologic coronary flow of subject-specific computer models were simulated. When we first simulated blood flow in complex subject-specific models with high mesh resolutions, however, we encountered instabilities in the outlet boundaries caused by complex flow structures, such as retrograde flow or complex flow propagating to the outlets from the interior domain due to vessel curvature or branches.

To resolve these instabilities, the invention further provides an augmented Lagrangian method to enforce the shape of the velocity profiles of the inlet boundary and the outlet boundaries with complex flow features or retrograde flow. The constraint functions enforce a shape of the velocity profile on a part of Neumann partition $\Gamma_{h_k}$ and minimize in-plane velocity components:

$$c_{k1}(\vec{v}, \vec{x}, t) = \alpha_k \int_{\Gamma_{h_k}} (\vec{v}(\vec{x}, t) \cdot \vec{n} - \Phi_k(\vec{v}(\vec{x}, t), \vec{x}, t))^2 ds = 0 \qquad (8)$$

$$\vec{x} \in \Gamma_{h_k}$$

$$c_{ki}(\vec{v}, \vec{x}, t) = \alpha_k \int_{\Gamma_{h_k}} (\vec{v}(\vec{x}, t) \cdot \vec{t}_i)^2 ds = 0 \text{ for } i = 2, 3$$

Here, $\Phi_k(\vec{v}(\vec{x},t),\vec{x},t)$ defines the shape of the normal velocity profile, $\vec{n}$ is the unit normal vector of face $\Gamma_{h_k}$. $\vec{t}_2$ and $\vec{t}_3$ are unit in-plane vectors which are orthogonal to each other and to the unit normal vector $\vec{n}$ at face $\Gamma_{h_k}$. $\alpha_k$ is used to nondimensionalize the constraint functions.

The boxed terms below are added to the weak form of the governing equations of blood flow and wall dynamics. The weak form becomes:

Find $\vec{v} \in \mathcal{S}$, $p \in \mathcal{P}$ and $\vec{\lambda}_1, \vec{\lambda}_2, \ldots, \vec{\lambda}_{n_c} \in (L^2(0,T))^{n_{sd}}$, $\vec{\kappa}_k \in \mathcal{R}^{n_{sd}^+}$, Penalty numbers where $k=1, \ldots, n_c$, and $\vec{\sigma}_k \in \mathcal{R}^{n_{sd}^+}$, Regularization parameters such that $|\vec{\sigma}_k| \ll 1$, $k=1, \ldots, n_c$ such that for any $\vec{w} \in W$, $q \in \mathcal{P}$ and $\delta\vec{\lambda}_1, \delta\vec{\lambda}_2, \ldots, \delta\vec{\lambda}_{n_c} \in (L^2(0,T))^{n_{sd}}$, the following is satisfied:

$$B_G(\vec{w}, q, \delta\vec{\lambda}_1, \ldots, \delta\vec{\lambda}_{n_c}; \vec{v}, p, \vec{\lambda}_1, \ldots, \vec{\lambda}_{n_c}) = \qquad (9)$$

$$\int_\Omega \left\{ \vec{w} \cdot \left(\rho \vec{v}_{,t} + \rho \vec{v} \cdot \nabla \vec{v} - \vec{f}\right) + \nabla \vec{w} : (-pI + \tau) \right\} d\vec{x} -$$

$$\int_\Omega \nabla q \cdot \vec{v} d\vec{x} - \int_{\Gamma_h} \vec{w} \cdot (-pI + \tau) \cdot \vec{n} ds + \int_\Gamma q \vec{v} \cdot \vec{n} ds +$$

$$\xi \int_{\Gamma_h^s} \left\{ \vec{w} \cdot \rho^s \vec{v}_{,t}^s + \nabla \vec{w} : \sigma^s(\vec{u}) - \vec{w} \cdot \vec{f}^s \right\} ds - \xi \int_{\partial \Gamma_h^s} \vec{w} \cdot \vec{h}^s dl +$$

$$\boxed{\sum_{i=1}^{n_{sd}} \sum_{k=1}^{n_c} \{\lambda_{ki} \cdot (\sigma_{ki} \delta \lambda_{ki} - \delta c_{ki}(\vec{w}; \vec{v}, \vec{x}, t))\} + \sum_{i=1}^{n_{sd}} \sum_{k=1}^{n_c} \delta\lambda_{ki} \cdot (\sigma_{ki} \lambda_{ki} - c_{ki}(\vec{v}, \vec{x}, t))} +$$

$$\boxed{\sum_{i=1}^{n_{sd}} \sum_{k=1}^{n_c} \kappa_{ki} \cdot c_{ki}(\vec{v}, \vec{x}, t) \delta c_{ki}(\vec{w}; \vec{v}, \vec{x}, t)} = 0$$

where $\delta c_{ki}(\vec{w}; \vec{v}, \vec{x}, t) = \lim_{\epsilon \to 0} \dfrac{d c_{ki}(\vec{v} + \epsilon \vec{w}, \vec{x}, t)}{d\epsilon}$ Here, $L^2(0,T)$ represents the Hilbert space of functions that are square-integrable in time [0,1]. Here $n_{sd}$ is the number of spatial dimensions and is assumed to be three and $n_c$ is the number of constrained surfaces. Here, in addition to the terms required to impose the augmented Lagrangian method, the regularization term $$\sum_{i=1}^{n_{sd}} \sum_{k=1}^{n_c} 2\sigma_{ki} \lambda_{ki} \delta\lambda_{ki}$$

is added to obtain a system of equations with a non-zero diagonal block for the Lagrange multiplier degrees of freedom. This method was shown not to alter the solution significantly except in the immediate vicinity of the constrained outlet boundaries and stabilize problems that previously diverged without constraints.

TABLE 1

Examples of parameter values of the closed loop system at rest and during exercise for the simulations of coronary flow and pressure with normal coronary anatomy. The examples are non-limiting to the invention

| | Rest | Exercise | | Rest | Exercise |
|---|---|---|---|---|---|
| Parameter values of the left and right sides of the heart | | | | | |
| $R_{LA-V}$ (dynes · s/cm$^5$) | 5 | 5 | $R_{RA-V}$ (dynes · s/cm$^5$) | 5 | 5 |
| $L_{LA-V}$ (dynes · s$^2$/cm$^5$) | 5 | 5 | $L_{RA-V}$ (dynes · s$^2$/cm$^5$) | 1 | 1 |
| $R_{LV-art}$ (dynes · s/cm$^5$) | 10 | 10 | $R_{RV-art}$ (dynes · s/cm$^5$) | 10 | 10 |
| $L_{LV-art}$ (dynes · s$^2$/cm$^5$) | 0.69 | 0.69 | $L_{RV-art}$ (dynes · s$^2$/cm$^5$) | 0.55 | 0.55 |
| $E_{LV,max}$ (mmHg/cc) | 2.0 | 2.0 | $E_{RV,max}$ (mmHg/cc) | 0.5 | 0.5 |
| $V_{LV,0}$ (cc) | 0 | 0 | $V_{RV,0}$ (cc) | 0 | 0 |
| $V_{LA,0}$ (cc) | −60 | −60 | $V_{RA,0}$ (cc) | −60 | −60 |
| $E_{LA}$ (mmHg/cc) | 270 | 350 | $E_{RA}$ (mmHg/cc) | 60 | 80 |
| Other parameter values | | | | | |
| $t_{max}$ (s) | 0.33 | 0.25 | Cardiac cycle (s) | 1.0 | 0.5 |
| $R_{pp}$ (dynes · s/cm$^5$) | 16 | 16 | $C_p$ (cm$^5$/dynes) | 0.022 | 0.022 |
| $R_{pd}$ (dynes · s/cm$^5$) | 144 | 144 | | | |

TABLE 2

Examples of parameter values of the three-element Windkessel models at rest and during exercise for the simulations of coronary flow and pressure with normal coronary anatomy. Note that the parameter values of the upper branch vessels are the same for the light exercise condition. The examples are non-limiting to the invention
Parameter values of the Windkessel models

| | B: Right subclavian | C: Right carotid | D: Right vertebral |
|---|---|---|---|
| $R_p$(10$^3$ dynes · s/cm$^5$) | 1.49 | 1.41 | 10.7 |
| C(10$^{-6}$ cm$^5$/dynes) | 235 | 248 | 32.9 |
| $R_d$(10$^3$ dynes · s/cm$^5$) | 15.1 | 14.3 | 108 |

| | E: Left carotid | F: Left vertebral | G: Left subclavian |
|---|---|---|---|
| $R_p$(10$^3$ dynes · s/cm$^5$) | 1.75 | 7.96 | 1.80 |
| C(10$^{-6}$ cm$^5$/dynes) | 201 | 44.0 | 195 |
| $R_d$(10$^3$ dynes · s/cm$^5$) | 17.6 | 80.5 | 18.2 |

| | H: Aorta (Rest) | H: Aorta (Exercise) |
|---|---|---|
| $R_p$(10$^3$ dynes · s/cm$^5$) | 0.227 | 0.180 |
| C(10$^{-6}$ cm$^5$/dynes) | 1540 | 1600 |
| $R_d$(10$^3$ dynes · s /cm$^5$) | 2.29 | 0.722 |

TABLE 3

Examples of parameter values of the lumped parameter models of the coronary vascular beds for the simulations of coronary flow and pressure with normal coronary anatomy. The examples are non-limiting to the invention.

| | $R_a$ | $R_{a\text{-}micro}$ | $R_v + R_{v\text{-}micro}$ | $C_a$ | $C_{im}$ |
|---|---|---|---|---|---|
| Parameter values of the coronary models at rest (Resistance in 10$^3$ dynes · s/cm$^5$ and capacitance in 10$^{-6}$ cm$^5$/dynes) | | | | | |
| a: LAD1 | 183 | 299 | 94 | 0.34 | 2.89 |
| b: LAD2 | 131 | 214 | 67 | 0.48 | 4.04 |
| c: LAD3 | 91 | 148 | 65 | 0.49 | 4.16 |
| d: LAD4 | 55 | 90 | 40 | 0.80 | 6.82 |
| e: LCX1 | 49 | 80 | 25 | 1.28 | 10.8 |
| f: LCX2 | 160 | 261 | 82 | 0.39 | 3.31 |
| g: LCX3 | 216 | 353 | 111 | 0.29 | 2.45 |
| h: LCX4 | 170 | 277 | 87 | 0.37 | 3.12 |
| i: RCA1 | 168 | 274 | 86 | 0.37 | 3.15 |
| j: RCA2 | 236 | 385 | 121 | 0.26 | 2.24 |
| k: RCA3 | 266 | 435 | 136 | 0.23 | 1.99 |

TABLE 3-continued

Examples of parameter values of the lumped parameter models of the coronary vascular beds for the simulations of coronary flow and pressure with normal coronary anatomy. The examples are non-limiting to the invention.

| | $R_a$ | $R_{a\text{-}micro}$ | $R_v + R_{v\text{-}micro}$ | $C_a$ | $C_{im}$ |
|---|---|---|---|---|---|
| Parameter values of the coronary models at exercise (Resistance in $10^3$dynes · s/cm$^5$ and capacitance in $10^{-6}$ cm$^5$/dynes) | | | | | |
| a: LAD1 | 76 | 24 | 18 | 0.75 | 6.88 |
| b: LAD2 | 52 | 16 | 13 | 1.02 | 9.34 |
| c: LAD3 | 51 | 16 | 12 | 1.07 | 9.74 |
| d: LAD4 | 31 | 10 | 7 | 0.74 | 15.9 |
| e: LCX1 | 20 | 6.2 | 5 | 2.79 | 25.4 |
| f: LCX2 | 65 | 20 | 15 | 0.85 | 7.78 |
| g: LCX3 | 87 | 27 | 21 | 0.63 | 5.74 |
| h: LCX4 | 68 | 21 | 16 | 0.80 | 7.29 |
| i: RCA1 | 71 | 22 | 16 | 0.83 | 7.60 |
| j: RCA2 | 98 | 31 | 23 | 0.59 | 5.38 |
| k: RCA3 | 110 | 35 | 25 | 0.52 | 4.72 |

What is claimed is:

1. A method for determining cardiovascular information for a patient, the method comprising:

receiving, using at least one computer system, patient-specific image data representing a first portion of a cardiovascular structure generated using non-invasive imaging techniques, wherein the first portion includes at least one coronary artery emanating from the patient's aorta;

receiving, using at least one computer system, patient-specific image data representing a second portion of the cardiovascular structure generated using non-invasive imaging techniques, wherein the second portion includes at least one coronary artery located downstream from the first portion;

creating, using at least one computer system, a three-spatial-dimension model of the first portion of the cardiovascular structure using the patient-specific image data, wherein the three-spatial-dimension model is associated with a first set of fluid dynamics equations representing the flow of fluid through the cardiovascular structure and comprising one or more parameters for blood flow rate, coronary blood pressure, and/or vessel wall displacement;

receiving, using at least one computer system, vessel morphology data generated using non-invasive imaging techniques;

receiving, using at least one computer system, at least one non-patient-specific resistance parameter value;

creating, using at least one computer system, a lumped-parameter coronary vascular model of the second portion of the cardiovascular structure using the vessel morphology data and the at least one non-patient-specific resistance parameter value, wherein the lumped-parameter coronary vascular model is associated with a second set of fluid dynamics equations comprising one or more parameters including at least one flow resistance parameter, and wherein the lumped-parameter coronary vascular model has less than three spatial dimensions;

generating, using at least one computer system, a modified model representing the first and second portions of the cardiovascular structure by coupling the three-spatial-dimension model of the first portion of the cardiovascular structure with the lumped-parameter coronary vascular model of the second portion of the cardiovascular structure, wherein the first set and second set of fluid dynamics equations associated with the three-spatial-dimension model and the lumped-parameter model are mathematically coupled;

calculating, using at least one computer system, one or more blood flow characteristics including blood flow rate, coronary blood pressure, and/or vessel wall displacement in the first portion of the cardiovascular structure using the modified model by simultaneously solving the mathematically coupled first set and second set of fluid dynamics equations associated with the modified model; and displaying, using at least one computer system, a visual representation based on the blood flow rate, coronary blood pressure, and/or vessel wall displacement.

2. The method of claim 1, further comprising:

modifying, using at least one computer system, the second set of fluid dynamics equations associated with the modified model based on a change in a physiological state of the patient, wherein the physiological state comprises a state of rest, a state of exercise, or a state of pharmacology-induced stress; and recalculating, using at least one computer system, one or more blood flow characteristics including blood flow rate, coronary blood pressure, and/or vessel wall displacement in the first portion of the cardiovascular structure using the modified model by simultaneously solving the mathematically coupled first set and second set of fluid dynamics equations associated with the modified model.

3. The method of claim 1, further comprising:

modifying, using at least one computer system, a parameter of the second set of fluid dynamics equations associated with the modified model; and recalculating, using at least one computer system, one or more blood flow characteristics including blood flow rate, coronary blood pressure, and/or vessel wall displacement in the first portion of the cardiovascular structure using the modified model by simultaneously solving the mathematically coupled first set and second set of fluid dynamics equations associated with the modified model.

4. A non-transitory computer readable medium for use on at least one computer system containing computer-executable programming instructions for performing a method for calculating cardiovascular information for a patient, the method comprising:

receiving, using at least one computer system, patient-specific image data representing a first portion of a cardiovascular structure generated using non-invasive imaging techniques, wherein the first portion includes at least one coronary artery emanating from the patient's aorta;

receiving, using at least one computer system, patient-specific image data representing a second portion of the cardiovascular structure generated using non-invasive imaging techniques, wherein the second portion includes at least one coronary artery located downstream from the first portion;

creating, using at least one computer system, a three-spatial-dimension model of the first portion of the cardiovascular structure using the patient-specific image data, wherein the three-spatial-dimension model is associated with a first set of fluid dynamics equations representing the flow of fluid through the cardiovascular structure and comprising one or more parameters for blood flow rate, coronary blood pressure, and/or vessel wall displacement;

receiving, using at least one computer system, vessel morphology data generated using non-invasive imaging techniques;

receiving, using at least one computer system, at least one non-patient-specific resistance parameter value;

creating, using at least one computer system, a lumped-parameter coronary vascular model of the second portion of the cardiovascular structure using the vessel morphology data and the at least one non-patient-specific resistance parameter value, wherein the lumped-parameter coronary vascular model is associated with a second set of fluid dynamics equations comprising one or more parameters including at least one flow resistance parameter, and wherein the lumped-parameter coronary vascular model has less than three spatial dimensions;

generating, using at least one computer system, a modified model representing the first and second portions of the cardiovascular structure by coupling the three-spatial-dimension model of the first portion of the cardiovascular structure with the lumped-parameter coronary vascular model of the second portion of the cardiovascular structure, wherein the first set and second set of fluid dynamics equations associated with the three-spatial-dimension model and the lumped-parameter model are mathematically coupled;

calculating, using at least one computer system, one or more blood flow characteristics including blood flow rate, coronary blood pressure, and/or vessel wall displacement in the first portion of the cardiovascular structure using the modified model by simultaneously solving the mathematically coupled first set and second set of fluid dynamics equations associated with the modified model; and displaying, using at least one computer system, a visual representation based on the blood flow rate, coronary blood pressure, and/or the vessel wall displacement.

5. The non-transitory computer readable medium of claim 4, wherein the at least one flow resistance parameter comprises at least one of a coronary arterial resistance parameter, a coronary arterial microcirculation resistance parameter, a coronary venous microcirculation resistance parameter, and a coronary venous resistance parameter.

6. The non-transitory computer readable medium of claim 4, wherein the lumped-parameter coronary vascular model includes at least one of a coronary arterial compliance parameter or a myocardial compliance parameter.

7. The non-transitory computer readable medium of claim 4, wherein the coronary blood pressure varies over time.

8. The non-transitory computer readable medium of claim 4, wherein the lumped-parameter coronary vascular model includes at least one of an atrial elastance parameter or a ventricular elastance parameter.

9. The non-transitory computer readable medium of claim 8, wherein at least one of the atrial elastance parameter or the ventricular elastance parameter varies over time.

10. The non-transitory computer readable medium of claim 4, wherein the lumped-parameter coronary vascular model includes an inductance parameter.

11. The method of claim 1, wherein:
the three-spatial-dimension model comprises a finite element model;
the three-spatial-dimension model comprises a plurality of coronary outlets that feed into the lumped-parameter coronary vascular model; and
the lumped-parameter coronary vascular model comprises resistance parameters implicitly coupled to one or more of the plurality of coronary outlets of the three-spatial-dimension model based on one or more equations of continuity of mass or momentum.

12. The non-transitory computer readable medium of claim 4, wherein:
the three-spatial-dimension model comprises a finite element model;
the three-spatial-dimension model comprises a plurality of coronary outlets that feed into the lumped-parameter coronary vascular model; and
the lumped-parameter coronary vascular model comprises resistance parameters implicitly coupled to one or more of the plurality of coronary outlets of the three-spatial-dimension model based on one or more equations of continuity of mass or momentum.

\* \* \* \* \*